(12) United States Patent
Plos et al.

(10) Patent No.: US 7,195,650 B2
(45) Date of Patent: *Mar. 27, 2007

(54) PROCESS FOR DYEING, WITH A LIGHTENING EFFECT, HUMAN KERATIN FIBERS THAT HAVE BEEN PERMANENTLY RESHAPED, USING AT LEAST ONE COMPOSITION COMPRISING AT LEAST ONE FLUORESCENT DYE

(75) Inventors: Grégory Plos, Paris (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 320 days.

This patent is subject to a terminal disclaimer.

(21) Appl. No.: 10/814,333

(22) Filed: Apr. 1, 2004

(65) Prior Publication Data

US 2005/0005368 A1    Jan. 13, 2005

Related U.S. Application Data

(60) Provisional application No. 60/468,104, filed on May 6, 2003.

(30) Foreign Application Priority Data

Apr. 1, 2003    (FR) ................... 03 04031

(51) Int. Cl.
*A61K 7/13*    (2006.01)
(52) U.S. Cl. ................ 8/405; 8/406; 8/407; 8/410; 8/411; 8/421; 8/648; 132/202; 132/208
(58) Field of Classification Search .......... 8/405, 8/406, 407, 410, 411, 421, 648, 658; 132/202, 132/208
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |

(Continued)

FOREIGN PATENT DOCUMENTS

| | | |
|---|---|---|
| AT | 302 534 | 10/1972 |
| CA | 1255603 | 6/1989 |
| CH | 487 231 | 3/1970 |
| DE | 33 13 332 | 10/1984 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |

(Continued)

OTHER PUBLICATIONS

"The Science of Hair Care" by Charles Zviak, 1998, Masson, pp. 215 & 278.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

A process for dyeing keratin fibers that have previously undergone a permanent reshaping process, comprising applying at least one composition comprising, in a cosmetically acceptable medium, at least one fluorescent dye that is soluble in the medium. The use of the at least one composition may makes it possible to dye a human keratin material, and further, for example, artificially dyed or pigmented hair, with a lightening effect.

25 Claims, No Drawings

U.S. PATENT DOCUMENTS

| | | | |
|---|---|---|---|
| 4,197,865 A | 4/1980 | Jacquet et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,240,450 A | 12/1980 | Grollier et al. | |
| 4,256,458 A | 3/1981 | Degen et al. | |
| 4,277,581 A | 7/1981 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,509,949 A | 4/1985 | Huang et al. | |
| 4,517,174 A * | 5/1985 | Jacquet et al. | 424/62 |
| 4,591,160 A | 5/1986 | Grollier | |
| 4,608,250 A | 8/1986 | Jacquet et al. | |
| 4,693,935 A | 9/1987 | Mazurek | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,781,724 A | 11/1988 | Wajaroff et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,961,925 A | 10/1990 | Tsujino et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,089,252 A | 2/1992 | Grollier et al. | |
| 5,139,037 A | 8/1992 | Grollier et al. | |
| 5,188,639 A | 2/1993 | Schultz et al. | |
| 5,196,189 A | 3/1993 | Jacquet et al. | |
| 5,275,808 A | 1/1994 | Murray et al. | |
| 5,316,551 A * | 5/1994 | Wenke | 8/406 |
| 5,356,438 A | 10/1994 | Kim et al. | |
| 5,445,655 A | 8/1995 | Kuhn et al. | |
| 5,635,461 A | 6/1997 | Onitsuka et al. | |
| 5,708,151 A | 1/1998 | Möckli | |
| 5,733,343 A | 3/1998 | Möckli | |
| 5,744,127 A * | 4/1998 | Giuseppe et al. | 424/59 |
| 5,792,221 A | 8/1998 | Lagrange et al. | |
| 5,830,446 A | 11/1998 | Berthiaume et al. | |
| 5,833,997 A | 11/1998 | Mahieu et al. | |
| 5,853,708 A | 12/1998 | Cauwet et al. | |
| 5,873,494 A | 2/1999 | Dallas, Jr. | |
| 5,958,392 A | 9/1999 | Grollier et al. | |
| 5,962,522 A | 10/1999 | Wacher et al. | |
| 6,106,577 A | 8/2000 | Audousset et al. | |
| 6,120,780 A | 9/2000 | Dupuis et al. | |
| 6,180,666 B1 | 1/2001 | Wacher et al. | |
| 6,260,556 B1 | 7/2001 | Legrand et al. | |
| 6,375,958 B1 | 4/2002 | Cauwet et al. | |
| 6,391,062 B1 * | 5/2002 | Vandenbossche et al. | 8/405 |
| 6,436,151 B2 | 8/2002 | Cottard et al. | |
| 6,436,153 B2 * | 8/2002 | Rondeau | 8/426 |
| 6,475,248 B2 | 11/2002 | Ohashi et al. | |
| 6,570,019 B2 | 5/2003 | Pasquier et al. | |
| 6,576,024 B1 | 6/2003 | Lang et al. | |
| 6,592,630 B2 | 7/2003 | Matsunaga et al. | |
| 6,616,709 B2 | 9/2003 | Ohashi et al. | |
| 6,712,861 B2 | 3/2004 | Rondeau | |
| 2001/0010812 A1 | 8/2001 | Chevalier et al. | |
| 2001/0023514 A1 | 9/2001 | Cottard et al. | |
| 2001/0023515 A1 | 9/2001 | Cottard et al. | |
| 2001/0031270 A1 | 10/2001 | Douin et al. | |
| 2001/0034914 A1 | 11/2001 | Saunier et al. | |
| 2001/0054206 A1 * | 12/2001 | Matsunaga et al. | 8/405 |
| 2001/0055580 A1 | 12/2001 | Belli et al. | |
| 2002/0004956 A1 | 1/2002 | Rondeau | |
| 2002/0012681 A1 | 1/2002 | George et al. | |
| 2002/0026676 A1 | 3/2002 | Ohashi et al. | |
| 2002/0046431 A1 | 4/2002 | Laurent et al. | |
| 2002/0046432 A1 | 4/2002 | Rondeau | |
| 2002/0088063 A1 | 7/2002 | Ohashi et al. | |
| 2002/0131941 A1 | 9/2002 | Habeck et al. | |
| 2002/0176836 A9 | 11/2002 | Belli et al. | |
| 2002/0176875 A9 | 11/2002 | Douin et al. | |
| 2003/0000023 A9 | 1/2003 | Rondeau | |
| 2003/0019052 A1 | 1/2003 | Pratt | |
| 2003/0019053 A9 | 1/2003 | Rondeau | |
| 2003/0055268 A1 | 3/2003 | Pasquier et al. | |
| 2003/0074747 A1 | 4/2003 | Vuarier et al. | |
| 2003/0124079 A1 | 7/2003 | Mougin et al. | |
| 2003/0131424 A1 | 7/2003 | Audousset et al. | |
| 2004/0019981 A1 | 2/2004 | Cottard et al. | |
| 2004/0034945 A1 | 2/2004 | Javet et al. | |
| 2004/0037796 A1 | 2/2004 | Cottard et al. | |
| 2004/0049860 A1 | 3/2004 | Cottard et al. | |
| 2004/0141943 A1 | 7/2004 | Mougin et al. | |
| 2004/0148711 A1 | 8/2004 | Rondeau | |
| 2004/0205901 A1 | 10/2004 | Cottard et al. | |
| 2004/0258641 A1 | 12/2004 | Plos et al. | |
| 2005/0005368 A1 | 1/2005 | Plos et al. | |
| 2005/0005369 A1 | 1/2005 | Plos et al. | |
| 2005/0008593 A1 | 1/2005 | Plos et al. | |
| 2005/0028301 A1 | 2/2005 | Pastore | |
| 2005/0144741 A1 | 7/2005 | Lang et al. | |

FOREIGN PATENT DOCUMENTS

| | | |
|---|---|---|
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 | 6/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |
| FR | 2411219 | 7/1979 |
| FR | 2416723 | 9/1979 |

| | | |
|---|---|---|
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2 692 572 | 12/1993 |
| FR | 2741261 | 5/1997 |
| FR | 2 773 864 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 759 385 | 10/1956 |
| GB | 1214394 | 1/1970 |
| GB | 1546809 | 5/1979 |
| GB | 1554331 | 10/1979 |
| GB | 746864 | 3/1985 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.
U.S. Appl. No. 10/742,995, filed Dec. 23, 2003.
U.S. Appl. No. 10/814,334, filed Apr. 1, 2004.
U.S. Appl. No. 10/814,430, filed Apr. 1, 2004.
U.S. Appl. No. 10/814,305, filed Apr. 1, 2004.
U.S. Appl. No. 10/814,300, filed Apr. 1, 2004.
U.S. Appl. No. 10/814,335, filed Apr. 1, 2004.
U.S. Appl. No. 10/814,428, filed Apr. 1, 2004.
U.S. Appl. No. 10/490,869, filed Apr. 1, 2004.
U.S. Appl. No. 10/814,236, filed Apr. 1, 2004.
U.S. Appl. No. 10/814,338, filed Apr. 1, 2004.
U.S. Appl. No. 10/814,337, filed Apr. 1, 2004.
U.S. Appl. No. 10/814,585, filed Apr. 1, 2004.
U.S. Appl. No. 10/814,336, filed Apr. 1, 2004.
English language Derwent Abstract for DE 33 13 332, published Oct. 18, 1984.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2,589,476 (EP 0 225 261) from EPO website.
English language Derwent Abstract for FR 2 773 864.
English language abstract from esp@cenet for FR 2 797 877.
English Language Derwent Abstract of FR 2,800,612.
English Language Abstract of FR 2 589 476 (EP 0 225 261) from EPO website.
English Language Derwent Abstract of JP 54-086521.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 8-259426.
English Language Derwent Abstract of JP 9-183714.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-220330.
English Language Derwent Abstract of JP 2001-261534.

English Language Derwent Abstract of JP 2001-294519.
English Language Derwent Abstract of JP 2001-302473.
English Language Derwent Abstract of JP 2001-516701.
English Language Derwent Abstract of JP 2001-516705.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2002-326911.
English Language Derwent Abstract of JP 2004-59468.
French Search Report for French Patent Application No. FR 02/16669, priority document for U.S. Appl. No. 10/742,995, filed Aug. 6, 2003.
French Search Report for French Patent Application No. FR 03/04021, priority document for U.S. Appl. No. 10/814,337, filed Dec. 8, 2003.
French Search Report for French Patent Application No. FR 03/04022, priority document for co-pending U.S. Appl. No. 10/814,336, filed Nov. 20, 2003.
French Search Report for French Patent Application No. FR 03/04024, priority document for co-pending U.S. Appl. No. 10/814,585, filed Dec. 8, 2003.
French Search Report for French Patent Application No. FR 03/04026, priority document for co-pending U.S. Appl. No. 10/814,335, filed Nov. 21, 2003.
French Search Report for French Patent Application No. FR 03/04027, priority document for co-pending U.S. Appl. No. 10/814,428, filed Nov. 28, 2003.
French Search Report for French Patent Application No. FR 03/04028, priority document for co-pending U.S. Appl. No. 10/814,236, filed Nov. 25, 2003.
French Search Report for French Patent Application No. FR 03/04029, priority document for co-pending U.S. Appl. No. 10/814,430, filed Feb. 5, 2004.
French Search Report for French Patent Application No. FR 03/04030, priority document for co-pending U.S. Appl. No. 10/814,300, filed Nov. 27, 2003.
French Search Report for French Patent Application No. FR 03/04031, priority document for co-pending U.S. Appl. No. 10/814,333, filed Jan. 8, 2004.
French Search Report for French Patent Application No. FR 03/04033, priority document for co-pending U.S. Appl. No. 10/814,334, filed Nov. 28, 2003.
French Search Report for French Patent Application No. FR 03/04034, priority document for co-pending U.S. Appl. No. 10/814,338, filed Feb. 17, 2004.
French Search Report for French Patent Application No. FR 03/04035, priority document for co-pending U.S. Appl. No. 10/814,305, filed Feb. 5, 2004.
International Search Report for PCT Application No. PCT/FR 02/03252, (for co-pending U.S. Appl. No. 10/490,869, filed Jan. 20, 2003.

Office Action mailed Nov. 2, 2005 in co-pending U.S. Appl. No. 10/814,338.
Office Action mailed Nov. 2, 2005 in co-pending U.S. Appl. No. 10/742,995.
Office Action mailed Nov. 3, 2005 in co-pending U.S. Appl. No. 10/490,869.
Office Action mailed Nov. 17, 2005 in co-pending U.S. Appl. No. 10/814,336.
Office Action mailed Mar. 15, 2006 in co-pending U.S. Appl. No. 10/814,337.
Office Action mailed Mar. 15, 2006 in co-pending U.S. Appl. No. 10/814,305.
Office Action mailed Mar. 23, 2006 in co-pending U.S. Appl. No. 10/814,300.
Office Action mailed Mar. 24, 2006 in co-pending U.S. Appl. No. 10/814,236.
Office Action mailed Mar. 27, 2006 in co-pending U.S. Appl. No. 10/814,334.
Office Action mailed May 25, 2006 in co-pending U.S. Appl. No. 10/814,335.
Office Action mailed May 26, 2006 in co-pending U.S. Appl. No. 10/490,869.
Office Action mailed May 30, 2006 in co-pending U.S. Appl. No. 10/814,338.
Office Action mailed Jun. 8, 2006 in co-pending U.S. Appl. No. 10/814,430.
Office Action mailed Jun. 21, 2006 in co-pending U.S. Appl. No. 10/814,336.
Office Action mailed Jul. 7, 2006 in co-pending U.S. Appl. No. 10/814,585.
Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).
Mishra, J.K. et al., "Synthesis of some bischromophoric dyes containing nonabsorbing flexible bridge," Indian Journal of Chemistry, vol. 31B, pp. 118-112, Feb. 1992.

* cited by examiner

PROCESS FOR DYEING, WITH A LIGHTENING EFFECT, HUMAN KERATIN FIBERS THAT HAVE BEEN PERMANENTLY RESHAPED, USING AT LEAST ONE COMPOSITION COMPRISING AT LEAST ONE FLUORESCENT DYE

This application claims benefit of U.S. Provisional Application No. 60/468,104, filed May 6, 2003.

Disclosed herein is a process for dyeing keratin fibers that have previously undergone a permanent reshaping process, using at least one composition comprising, in a cosmetically acceptable medium, at least one fluorescent dye that is soluble in the cosmetically acceptable medium.

In the field of haircare, it is common to need to perform permanent shaping and dyeing steps with only a short time interval, or even immediately one after the other, the shaping operation being performed as the first step. However, such processes may damage the keratin fibers.

For example, one of the conventional processes for reshaping the hair comprises two steps, wherein the first step comprises reducing the disulphide bridges present in the keratin fiber, by using at least one reducing agent. Once these disulphide bridges have been reduced, the hair may then be shaped as desired. This shaping may comprise curling the hair or smoothing it out, the result depending on the means used to place the hair under tension. This tensioning operation may be performed before, during or after applying the reducing composition. Once this first step has been performed, an oxidation step is necessary in order to recreate the disulphide bridges and to stabilize the shape obtained. This operation may be performed in an oxidizing medium.

There is another process for permanently reshaping the hair, which may be applicable, for example, in the case of relaxing the hair, and which may comprise applying to the head of hair, while smoothing it out, a concentrated alkali metal hydroxide solution. During this operation, the keratin fibers may become relatively damaged since it is partially dissolved in the alkaline solution. Once this treatment has been performed, the hair is rinsed.

It is thus clear that, after treatments of this type, the keratin fibers may be relatively damaged or embrittled and the implementation of a subsequent coloring step may represent a further risk of degradation, this risk being all the more pronounced when it is desired to lighten the fibers.

For example, dyeing processes may be performed in the presence of at least one oxidizing agent, in an alkaline medium. Furthermore, these conditions may be proportionately harsher the greater the desired degree of lightening of the hair.

Thus, the present inventors have proposed a process for dyeing the hair with a lightening effect, performed subsequent to a process for permanently reshaping the hair, which may not substantially contribute towards further degradation of the treated fibers.

It has thus been found that the use of fluorescent dyes, for example, those in the orange range, used after a process for permanently reshaping keratin fibers, may make it possible to obtain uniform aesthetic colorations with at least one good fastness property with respect to external agents, for example, shampooing.

Disclosed herein is thus a process for dyeing, with a lightening effect, human keratin fibers that have previously been subjected to a permanent reshaping process, comprising:

a) applying at least one composition comprising, in a cosmetically acceptable medium, at least one fluorescent dye that is soluble in the medium;

b) leaving the at least one composition on the keratin fibers to act for a time period sufficient to develop a desired coloration and lightening;

b) optionally rinsing the keratin fibers;

c) optionally washing the keratin fibers with shampoo and optionally rinsing the keratin fibers; and d) drying or leaving to dry the keratin fibers.

However, other characteristics and advantages of the embodiments disclosed herein will emerge more clearly on reading the description and the example that follow.

Unless otherwise indicated, the limits of the ranges of values that are given in the description are included in these ranges.

For the purpose of clarity in the description, the at least one composition used in step a) will first be described.

As has been mentioned previously, the at least one composition comprises at least one fluorescent dye which is soluble in the medium of the at least one composition.

As used herein, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

The at least one fluorescent dye disclosed herein is to be differentiated from an optical brightener. Optical brighteners, which are also known as brighteners, fluorescent brighteners, fluorescent brightening agents, fluorescent whitening agents, whiteners or fluorescent whiteners, are colorless transparent compounds. Optical brighteners do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum. The color impression is then generated solely by purely fluorescent light that is predominantly blue (wavelengths ranging from 400 to 500 nanometers).

Finally, the at least one fluorescent dye used in the at least one composition is soluble in the medium of the at least one composition. It should be pointed out that the at least one fluorescent dye differs from a fluorescent pigment, which itself is insoluble in the medium of the at least one composition.

In one embodiment, the at least one fluorescent dye used in the at least one composition, which is optionally neutralized, is soluble in the medium of the at least one composition to at least 0.001 g/l, for example, to at least 0.5 g/l, further, for example, to at least 1 g/l and, even further, for example, to at least 5 g/l at a temperature ranging from 15 to 25° C.

The at least one fluorescent dye which may be used can be, for example, chosen from dyes in the orange range.

For example, the at least one fluorescent dye may lead to a reflectance maximum that is in the wavelength range of from 500 to 650 nanometers and, for example, in the wavelength range of from 550 to 620 nanometers.

The at least one fluorescent dye may be chosen from compounds that are known per se.

For example, the at least one fluorescent dye that may be used may be chosen from naphthalimides; cationic and non-cationic coumarins; xanthenodiquinolizines (such as sulphorhodamines); azaxanthenes; naphtholactams; azlactones; oxazines; thiazines; dioxazines; azo, azomethine and methine monocationic, and azo, azomethine and methine polycationic fluorescent dyes. For example, the at least one fluorescent dye may be chosen from naphthalimides; cationic and non-cationic coumarins; azaxanthenes; naphtholactams; azlactones; oxazines; thiazines; dioxazines; azo, azomethine and methine monocationic fluorescent dyes, and azo, azomethine and methine polycationic fluorescent dyes.

For example, the at least one fluorescent dye may be chosen from:

compounds having the following structure:

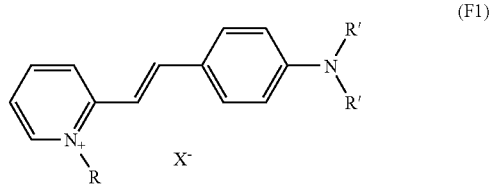

wherein R is chosen from methyl and ethyl radicals; R' is a methyl radical; and $X^-$ is chosen from anions such as iodide, sulphate and methosulphate.

An example of a compound of this type is Photosensitizing Dye NK-557 sold by the company Ubichem, wherein R is an ethyl radical, R' is a methyl radical and $X^-$ is iodide. Brilliant Yellow B6GL sold by the company Sandoz and having the following formula (F2):

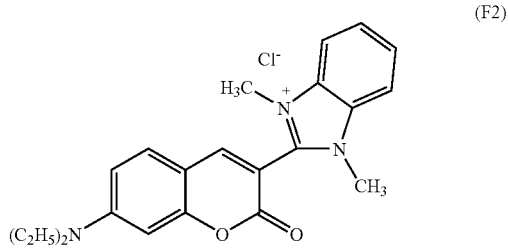

Basic Yellow 2, and Auramine O, sold by the companies Prolabo, Aldrich and Carlo Erba and having the following formula (F3):

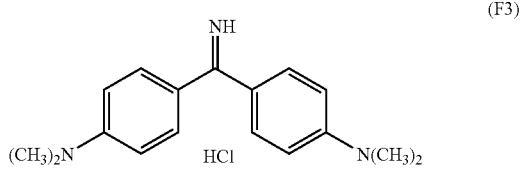

4,4'-(imidocarbonyl)bis(N,N-dimethylaniline) monohydrochloride—CAS number 2465-27-2.

Further examples include compounds having the following formula (F4):

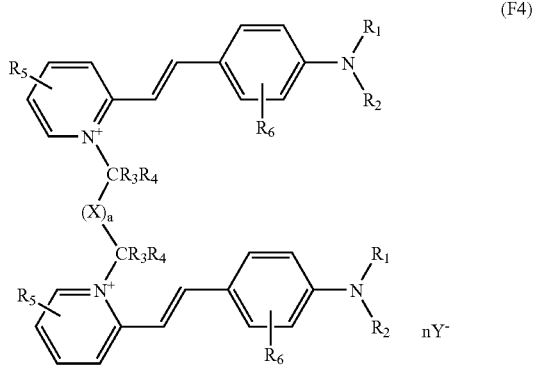

wherein:

$R_1$ and $R_2$, which may be identical or different, are each chosen from:

a hydrogen atom;

linear and branched alkyl radicals comprising from 1 to 10 carbon atoms, such as, from 1 to 4 carbon atoms, wherein said alkyl radicals are optionally interrupted and/or substituted with at least one entity chosen from hetero atoms and from groups comprising at least one hetero atom and/or wherein said alkyl radicals are substituted with at least one halogen atom;

aryl and arylalkyl radicals, wherein the aryl group comprises 6 carbon atoms and the alkyl group comprises from 1 to 4 carbon atoms; wherein the aryl radical is optionally substituted with at least one radical chosen from linear and branched alkyl radicals comprising from 1 to 4 carbon atoms, wherein the at least one radical is optionally interrupted and/or substituted with at least one entity chosen from hetero atoms and from groups comprising at least one hetero atom and/or wherein the at least one radical is optionally substituted with at least one halogen atom;

$R_1$ and $R_2$ may optionally form, together with the nitrogen atom to which they are attached, a heterocycle and may comprise at least one other hetero atom, wherein the heterocycle is optionally substituted with at least one alkyl radical chosen from linear and branched alkyl radicals comprising, for example, from 1 to 4 carbon atoms, wherein the at least one alkyl radical is optionally interrupted and/or substituted with at least one entity chosen from hetero atoms and groups comprising at least one hetero atom and/or wherein the at least one alkyl radical is optionally substituted with at least one halogen atom; and $R_1$ or $R_2$ may optionally form together with the nitrogen to which it is attached and one of the carbon atoms of the phenyl group bearing the nitrogen atom, a heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; and linear and branched alkyl radicals comprising from 1 to 4 carbon atoms, wherein the alkyl radicals are optionally substituted and/or interrupted with at least one entity chosen from hetero atoms and groups bearing at least one hetero atom and/or wherein the alkyl radicals are optionally substituted with at least one halogen atom;

X is chosen from:

linear and branched alkyl radicals comprising from 1 to 14 carbon atoms and alkenyl radicals comprising from 2 to 14 carbon atoms, wherein the alkyl radicals and the alkenyl radicals are optionally interrupted and/or substituted with at least one entity chosen from hetero atoms and from groups comprising at least one hetero atom and/or wherein said radicals are optionally substituted with at least one halogen atom;

5- or 6-membered heterocyclic radicals optionally substituted with at least one alkyl radical chosen from linear and branched alkyl radicals comprising from 1 to 14 carbon atoms, wherein the at least one alkyl radical is optionally substituted with at least one entity chosen from hetero atoms; with linear and branched aminoalkyl radicals comprising from 1 to 4 carbon atoms, optionally substituted with at least one hetero atom; and/or with at least one halogen atom;

fused and non-fused aromatic and diaromatic radicals, optionally separated with at least one alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one entity chosen from hetero atoms and from groups bearing at least one hetero atom;

a dicarbonyl radical; and wherein the group X possibly bears at least one cationic charge;

a is equal to 0 or 1;

$Y^-$, which may be identical or different, is chosen from organic and mineral anions;

n is an integer equal to at least 2 and at most equal to the number of cationic charges present in the at least one fluorescent dye.

As used herein, the term "hetero atom" means an oxygen or nitrogen atom.

Examples of groups bearing such atoms include, inter alia, hydroxyl, alkoxy, carbonyl, amino, ammonium, amido (—N—CO—) and carboxyl (—O—CO— or —CO—O—) groups.

As used herein, the term "alkenyl groups" means groups that comprise at least one unsaturated carbon-carbon bond (—C=C—) and, for example, only one carbon-carbon double bond.

In formula (F4), the radicals $R_1$ and $R_2$, which may be identical or different, may, for example, be chosen from:

a hydrogen atom;

alkyl radicals comprising from 1 to 10 carbon atoms, for example, from 1 to 6 carbon atoms and, further, for example, from 1 to 4 carbon atoms, optionally interrupted with an oxygen atom and/or optionally substituted with at least one entity chosen from hydroxyl, amino and ammonium radicals and from chlorine and fluorine atoms; and benzyl and phenyl radicals optionally substituted with at least one radical chosen from alkyl and alkoxy radicals comprising from 1 to 4 carbon atoms and, for example, comprising 1 or 2 carbon atoms;

$R_1$ and $R_2$ may form, together with the nitrogen atom to which they are attached, at least one heterocyclic radical chosen from pyrrolo, pyrrolidino, imidazolino, imidazolo, imidazolium, pyrazolino, piperazino, morpholino, morpholo, pyrazolo and triazolo heterocyclic radicals, optionally substituted with at least one alkyl radical chosen from linear and branched alkyl radicals comprising from 1 to 4 carbon atoms optionally interrupted and/or substituted with at least one entity chosen from nitrogen and oxygen atoms and from groups bearing at least one atom chosen from nitrogen and oxygen atoms.

With regard to the abovementioned amino and ammonium radicals, the radicals borne by the nitrogen atom may be identical or different and may, for example, be chosen from a hydrogen atom, $C_1$–$C_{10}$, for example, $C_1$–$C_4$, alkyl radicals and arylalkyl radicals wherein, for example, the aryl radical comprises 6 carbon atoms and the alkyl radical comprises from 1 to 10 carbon atoms and, for example, from 1 to 4 carbon atoms.

In one embodiment, the radicals $R_1$ and $R_2$, which may be identical or different, may each be chosen from a hydrogen atom; linear and branched $C_1$–$C_6$ alkyl radicals; $C_2$–$C_6$ alkyl radicals substituted with at least one hydroxyl radical; $C_2$–$C_6$ alkyl radicals bearing at least one group chosen from amino and ammonium groups; $C_2$–$C_6$ chloroalkyl radicals; $C_2$–$C_6$ alkyl radicals interrupted with at least one entity chosen from an oxygen atom and from groups bearing at least one oxygen atom, for example, an ester group; aromatic radicals, for example, phenyl, benzyl and 4-methylphenyl; heterocyclic radicals such as pyrrolo, pyrrolidino, imidazolo, imidazolino, imidazolium, piperazino, morpholo, morpholino, pyrazolo and triazolo radicals, optionally substituted with at least one radical chosen from $C_1$–$C_6$ alkyl and aromatic radicals.

In another embodiment, the radicals $R_1$ and $R_2$, which may be identical or different, may each be chosen from a hydrogen atom, linear and branched $C_1$–$C_6$ alkyl radicals such as methyl, ethyl, n-butyl and n-propyl radicals; 2-hydroxyethyl; alkyltrimethylammonium and alkyltriethylammonium radicals, wherein the alkyl radical is chosen from linear $C_2$–$C_6$ alkyl radicals; (di)alkylmethylamino and (di)alkylethylamino radicals, wherein the alkyl radical is chosen from linear $C_1$–$C_6$ alkyl radicals; —$CH_2CH_2Cl$; —$(CH_2)_n$—$OCH_3$ and —$(CH_2)_n$—$OCH_2CH_3$ wherein n is an integer ranging from 2 to 6; —$CH_2CH_2$—$OCOCH_3$; and —$CH_2CH_2COOCH_3$.

For example, the radicals $R_1$ and $R_2$, which may be identical or different, and in one embodiment may be identical, may be chosen from a methyl radical and an ethyl radical.

The radicals $R_1$ and $R_2$, which may be identical or different, may also be chosen from pyrrolidino, 3-aminopyrrolidino, 3-(dimethyl)aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo heterocyclic radicals.

The radicals $R_1$ and $R_2$, which may be identical or different, may also form a heterocycle chosen from heterocycles of formulae (I) and (II) below:

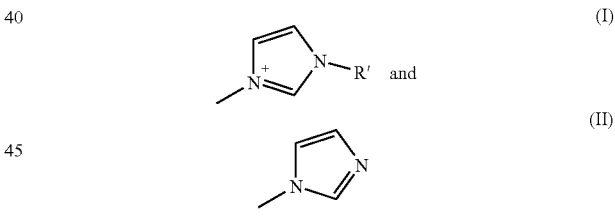

wherein R' is chosen from a hydrogen atom, $C_1$–$C_3$ alkyl radicals, —$CH_2CH_2OH$, and —$CH_2CH_2OCH_3$.

In another embodiment, $R_5$, which may be identical or different, may be chosen from a hydrogen atom, a fluorine atom, a chlorine atom, and linear and branched alkyl radicals comprising from 1 to 4 carbon atoms optionally interrupted with at least one atom chosen from oxygen and nitrogen atoms.

The substituent $R_5$, if it is not a hydrogen atom, may, for example, be in at least one position chosen from 3 and 5 relative to the carbon of the ring bearing the nitrogen substituted with the radicals $R_1$ and $R_2$, and may, for example, be in position 3 relative to that carbon.

For example, the radicals $R_5$, which may be identical or different, may each be chosen from a hydrogen atom; linear and branched $C_1$–$C_4$ alkyl radicals; —O—$R_{51}$ wherein $R_{51}$ is chosen from linear $C_1$–$C_4$ alkyl radicals; —$R_{52}$—O—$CH_3$ wherein $R_{52}$ is chosen from linear $C_2$–$C_3$ alkyl radicals;

—$R_{53}$—$N(R_{54})_2$ wherein $R_{53}$ is chosen from linear $C_2$–$C_3$ alkyl radicals and $R_{54}$, which may be identical or different, is chosen from a hydrogen atom and a methyl radical.

For example, $R_5$, which may be identical or different, may be chosen from a hydrogen atom and methyl and methoxy radicals. In one embodiment, $R_5$ may be a hydrogen atom.

In another embodiment, the radicals $R_6$, which may be identical or different, may be chosen from a hydrogen atom; linear and branched $C_1$–$C_4$ alkyl radicals; —X wherein X is chosen from chlorine, bromine and fluorine atoms; —$R_{61}$—O—$R_{62}$ wherein $R_{61}$ is chosen from linear $C_2$–$C_3$ alkyl radicals and $R_{62}$ is a methyl radical; —$R_{63}$—$N(R_{64})_2$ wherein $R_{63}$ is chosen from linear $C_2$–$C_3$ alkyl radicals and $R_{64}$, which may be identical or different, is chosen from a hydrogen atom and a methyl radical; —$N(R_{65})_2$ wherein $R_{65}$, which may be identical or different, is chosen from a hydrogen atom and linear $C_2$–$C_3$ alkyl radicals; —NH-$COR_{66}$ wherein $R_{66}$. is chosen from $C_1$–$C_2$ alkyl radicals, $C_1$–$C_2$ chloroalkyl radicals, radicals —$R_{67}$—$NH_2$, —$R_{67}$—$NH(CH_3)$, —$R_{67}$—$N(CH_3)_2$, —$R_{67}$—$N^+(CH_3)_3$, and —$R_{67}$—$N^+(CH_2CH_3)_3$ wherein $R_{67}$ is chosen from $C_1$–$C_2$ alkyl radicals.

The substituent $R_6$, if it is not a hydrogen atom, may, for example, be in at least one position chosen from positions 2 and 4 relative to the nitrogen atom of the pyridinium ring, and, in one embodiment, may be in position 4 relative to the nitrogen atom.

For example, the radicals $R_6$, which may be identical or different, may be chosen from a hydrogen atom and methyl and ethyl radicals, and $R_6$ may, for example, be a hydrogen atom.

With regard to the radicals $R_3$ and $R_4$, these radicals, which may be identical or different, may each, for example, be chosen from a hydrogen atom and alkyl radicals comprising from 1 to 4 carbon atoms and, for example, a methyl radical. For example, $R_3$ and $R_4$ may each be a hydrogen atom.

As mentioned above, X may be chosen from:
- linear and branched alkyl radicals comprising from 1 to 14 carbon atoms and alkenyl radicals comprising from 2 to 14 carbon atoms, wherein the alkyl radicals and the alkenyl radicals are optionally interrupted and/or substituted with at least one entity chosen from hetero atoms and from groups comprising at least one hetero atom and/or wherein the radicals are substituted with at least one halogen atom;
- 5- or 6-membered heterocyclic radicals optionally substituted with at least one alkyl radical chosen from linear and branched alkyl radicals comprising from 1 to 14 carbon atoms, optionally substituted with at least one hetero atom; with linear and branched aminoalkyl radicals comprising from 1 to 4 carbon atoms, optionally substituted with at least one hetero atom; and/or with at least one halogen atom;
- fused and non-fused aromatic and diaromatic radicals, optionally separated with at least one alkyl radical comprising from 1 to 4 carbon atoms, wherein the aromatic and diaromatic radicals are optionally substituted with at least one entity chosen from halogen atoms and alkyl radicals comprising from 1 to 10 carbon atoms optionally substituted and/or interrupted with at least one entity chosen from hetero atoms and from groups bearing at least one hetero atom; and
- a dicarbonyl radical.

In addition, the group X may bear at least one cationic charge.

Thus, X may be chosen from linear and branched alkyl radicals comprising from 1 to 14 carbon atoms and alkenyl radicals comprising from 2 to 14 carbon atoms, wherein the alkyl radicals and the alkenyl radicals may be substituted and/or interrupted with at least one entity chosen from oxygen and nitrogen atoms, from groups bearing at least one hetero atom, and from fluorine and chlorine atoms.

Examples of such groups include hydroxyl, alkoxy (for example, having from 1–4 carbon atoms), amino, ammonium, amido, carbonyl and carboxyl groups (—COO— or —O—CO—) for example, with an alkyloxy radical.

It should be noted that the nitrogen atom, if it is present, may be in a quaternized or non-quaternized form. In this case, the other radical or the other two radicals borne by the quaternized or non-quaternized nitrogen atom may be identical or different and may be chosen from a hydrogen atom and $C_1$–$C_4$ alkyl radicals, for example, a methyl radical.

According to another embodiment, the group X is chosen from 5- and 6-membered heterocyclic imidazolo, pyrazolo, triazino and pyridino radicals, optionally substituted with at least one linear or branched alkyl radical comprising from 1 to 14 carbon atoms, for example, from 1 to 10 carbon atoms and, for example, from 1 to 4 carbon atoms; with at least one linear or branched aminoalkyl radical comprising from 1 to 10 carbon atoms and, for example, from 1 to 4 carbon atoms, optionally substituted with at least one group comprising at least one hetero atom (for example, at least one hydroxyl radical); and/or optionally substituted with a halogen atom. For example, the amino group may be linked to the heterocycle.

In yet another embodiment, the group X is chosen from aromatic radicals (for example, comprising 6 carbon atoms) and fused and non-fused diaromatic radicals (for example, comprising from 10 to 12 carbon atoms), possibly separated with at least one alkyl radical comprising 1 to 4 carbon atoms, wherein the aromatic and diaromatic radicals are optionally substituted with at least one entity chosen from a halogen atom and alkyl radicals comprising from 1 to 10 carbon atoms and, for example, from 1 to 4 carbon atoms, wherein said alkyl radicals are optionally interrupted with at least one entity chosen from oxygen and nitrogen atoms and from groups comprising at least one hetero atom, for example, carbonyl, carboxyl, amido, amino and ammonium radicals.

It should be noted that the aromatic radical, for example, a phenyl radical, is linked to the groups $CR_3R_4$ via bonds in positions 1,2; 1,3 or 1,4 and, for example, in positions 1,3 and 1,4. If the phenyl radical linked via bonds in positions 1,4 bears one or two substituents, this or these substituent(s) may, for example, be located in position 1,4 relative to one of the groups $CR_3R_4$. If the phenyl radical linked via bonds in positions 1,3 bears one or two substituents, this or these substituents may, for example, be located in position 1 and/or 3 relative to one of the groups $CR_3R_4$.

When the radical is diaromatic, it may, for example, be non-fused and comprise two phenyl radicals possibly separated with a single bond (i.e., a carbon of each of the two rings) or with at least one alkyl radical, for example, a $CH_2$ or $C(CH_3)_2$ alkyl radical. In one embodiment, the aromatic radicals do not bear a substituent. It should be noted that the diaromatic radical is linked to the groups $CR_3R_4$ via bonds in positions 4,4'.

Examples of group X include linear and branched alkyl radicals comprising from 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals substituted and/ or interrupted with at least one entity chosen from nitrogen and oxygen atoms and from groups bearing at least one hetero atom (hydroxyl, amino, ammonium, carbonyl and carboxyl, for example), such as —CH$_2$CH$_2$OCH$_2$CH$_2$—, 1,6-dideoxy-d-mannitol, —CH$_2$N$^+$(CH$_3$)$_2$CH$_2$—, —CH$_2$CH$_2$N$^+$(CH$_3$)$_2$—(CH$_2$)$_6$N$^+$(CH$_3$)$_2$—CH$_2$CH$_2$—, CO—CO—, 3,3-dimethylpentylene, 2-acetoxyethylene, butylene-1,2,3,4-tetraol; —CH═CH—; aromatic and diaromatic radicals substituted with at least one entity chosen from alkyl radicals, from groups bearing at least one atom chosen from hetero atoms and from at least one halogen atom, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; heterocyclic radicals such as pyridine, and derivatives such as 2,6-bispyridine, imidazole, imidazolium and triazine.

In another embodiment, X is chosen from linear and branched C$_1$–C$_{13}$ alkyl radicals; —CH$_2$CH(OH)CH$_2$—; —CH$_2$CH(Cl)CH$_2$—; —CH$_2$CH$_2$—OCOCH$_2$—; —CH$_2$CH$_2$COOCH$_2$—; and —Ra—O—Rb— wherein Ra is chosen from linear C$_2$–C$_6$ alkyl radicals and Rb is chosen from linear C$_1$–C$_2$ alkyl radicals; —Rc—N(Rd)—Re— wherein Rc is chosen from C$_2$–C$_9$ alkyl radicals, Rd is chosen from a hydrogen atom and C$_1$–C$_2$ alkyl radicals and Re is chosen from C$_1$–C$_6$ alkyl radicals; —Rf—N$^+$(Rg)$_2$—Rh— wherein Rf is chosen from linear C$_2$–C$_9$ alkyl radicals, Rg, which may, for example, be identical, is chosen from C$_1$–C$_2$ alkyl radicals and Rh is chosen from linear C$_1$–C$_6$ alkyl radicals; and —CO—CO—.

X may be an imidazole radical, optionally substituted with at least one alkyl radical comprising from 1 to 14 carbon atoms, for example, from 1 to 10 carbon atoms and, for example, from 1 to 4 carbon atoms wherein, for example, X may be chosen from divalent radicals having the following formula;

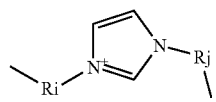

(III)

wherein Ri and Rj, which may be identical or different, are each chosen from linear C$_1$–C$_6$ alkyl radicals;

X may similarly be chosen from the divalent triazine-based radicals below:

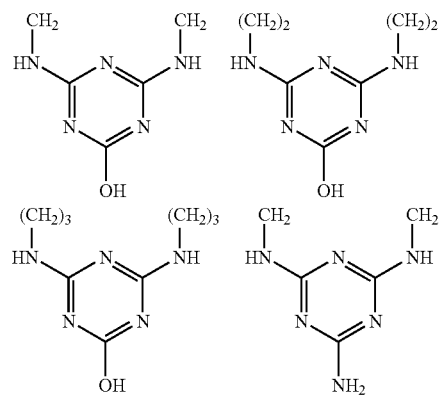

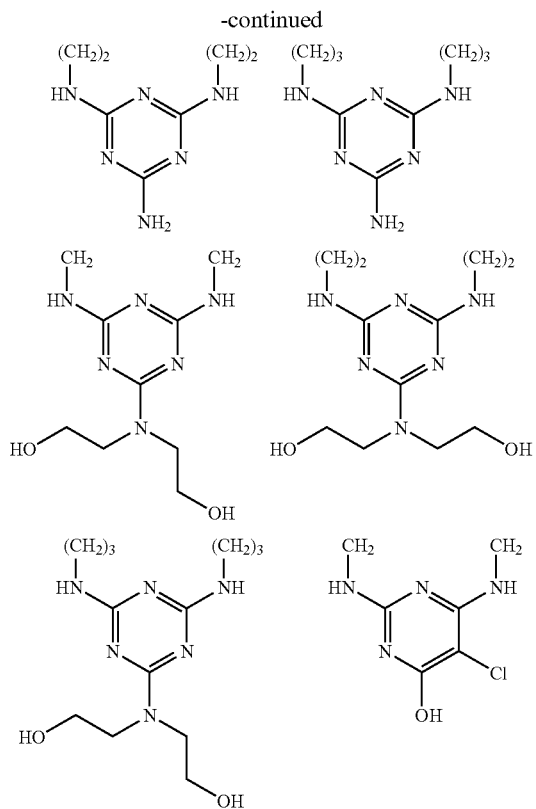

X may also, for example, be chosen from the divalent aromatic radicals below:

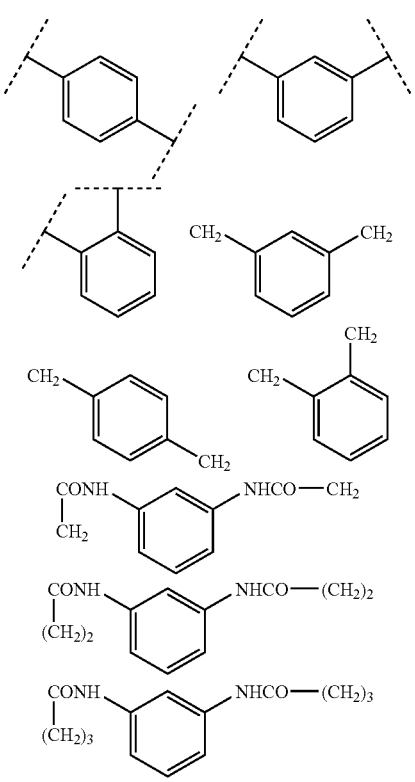

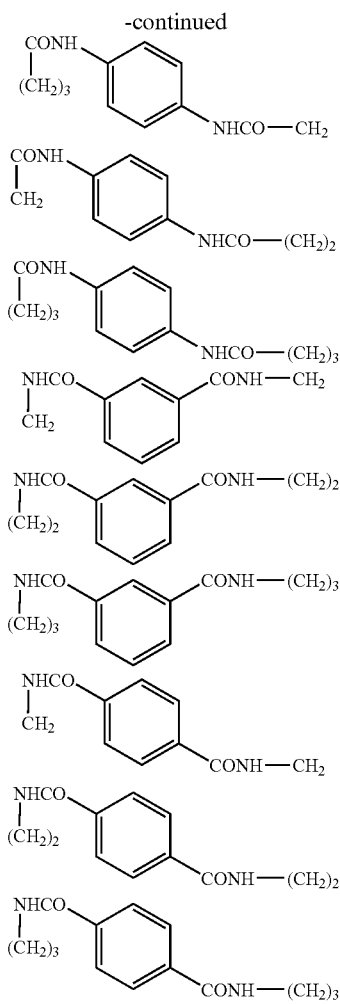

In formula (F4), Y⁻ is chosen from organic and mineral anions. If there are several anions Y⁻, these anions may be identical or different.

Non-limiting examples of anions of mineral origin include anions derived from halogen atoms, such as chlorides, and iodides, sulphates and bisulphates, nitrates, phosphates, hydrogen phosphates, dihydrogen phosphates, carbonates and bicarbonates.

Non-limiting examples of anions of organic origin include anions derived from the salts of saturated and unsaturated, aromatic and non-aromatic monocarboxylic and polycarboxylic, sulphonic and sulphuric acids, optionally substituted with at least one entity chosen from hydroxyl and amino radicals, and halogen atoms. Further non-limiting examples include acetates, hydroxyacetates, aminoacetates, (tri)chloroacetates, benzoxyacetates, propionates and derivatives thereof bearing at least one chlorine atom, fumarates, oxalates, acrylates, malonates, succinates, lactates, tartrates, glycolates, citrates, benzoates and derivatives thereof bearing at least one radical chosen from methyl and amino radicals, alkyl sulphates, tosylates, benzenesulphonates, and toluene-sulphonates.

For example, the anion(s) Y, which may be identical or different, may be chosen from chloride, sulphate, methosulphate and ethosulphate.

Finally, the integer n is at least equal to 2 and at most equal to the number of cationic charges present in the at least one fluorescent dye.

For example, the at least one fluorescent dye that has just been described in detail is a symmetrical compound.

The at least one fluorescent dye may be synthesized by reacting, in a first step, α-picoline with a reagent comprising two leaving groups that may be chosen from halogen atoms, for example, bromine, and optionally chlorine, and tolylsulphonyl and methanesulphonyl groups.

This first step may take place in the presence of a solvent, although this is not obligatory, for example, dimethylformamide.

The number of moles of α-picoline is generally in the region of 2 per mole of reagent comprising the leaving groups.

In addition, the reaction is usually performed at the reflux temperature of the reagent and/or of the solvent if a solvent is present.

The product derived from this first step is then placed in contact with a corresponding aldehyde having the following formula:

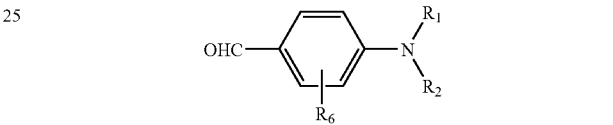

wherein $R_1$, $R_2$ and $R_6$ have the same meanings as indicated above.

In this case also, the reaction may be performed in the presence of a suitable solvent, which may, for example, be at reflux.

It should be noted that the radicals $R_1$ and $R_2$ of the aldehyde may have the meaning indicated in formula (F4) detailed previously.

It is also possible to use an aldehyde for which the radicals, $R_1$ and $R_2$, are hydrogen atoms and to perform, in accordance with standard methods, the substitution of these hydrogen atoms with suitable radicals as described in formula (F4) once the second step is complete.

Reference may be made, for example, to syntheses as described in U.S. Pat. No. 4,256,458, the disclosure of which is incorporated by reference herein.

The at least one fluorescent dye may be present in the composition disclosed herein in an amount ranging from 0.01% to 20% by weight, for example, from 0.05% to 10% by weight, and further, for example, from 0.1% to 5% by weight, relative to the total weight of the composition.

The cosmetically acceptable medium may, for example, be chosen from water and mixtures of water and at least one common organic solvent.

The at least organic solvent may, for example, be chosen from alcohols such as ethyl alcohol, isopropyl alcohol, benzyl alcohol and phenylethyl alcohol, and glycols and glycol ethers, for example, ethylene glycol monomethyl ether, monoethyl ether and monobutyl ether, propylene glycol and ethers thereof, for example, propylene glycol monomethyl ether, butylene glycol, dipropylene glycol and diethylene glycol alkyl ethers, for example, diethylene glycol monoethyl ether and monobutyl ether, and polyols, for example, glycerol. Polyethylene glycols and polypropylene glycols, and mixtures of all these compounds, may also be used as the at least one organic solvent.

The at least one organic solvent, if present, is present in an amount ranging from 1% to 40% by weight and, for example, from 5% to 30% by weight, relative to the total weight of the at least one composition.

The pH of the at least one composition may, for example, range from 3 to 12 and further, for example, from 5 to 11.

It may be adjusted to the desired value by means of acidifying or basifying agents.

Examples of acidifying agents that may be used include mineral and organic acids, for example, hydrochloric acid, orthophosphoric acid, sulphuric acid, carboxylic acids, for example, acetic acid, tartaric acid, citric acid and lactic acid, and sulphonic acids.

Examples of basifying agents include aqueous ammonia, alkaline carbonates, alkanolamines such as monoethanolamine, diethanolamine and triethanolamine and derivatives thereof, sodium hydroxide, potassium hydroxide and the compounds of formula (A) below:

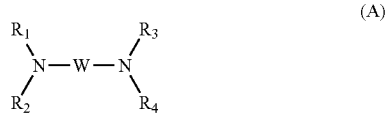

(A)

wherein W is chosen from propylene residues optionally substituted with at least one entity chosen from hydroxyl groups and $C_1$–$C_6$ alkyl radicals; $R_1$, $R_2$, $R_3$ and $R_4$, which may be identical or different, are each chosen from a hydrogen atom and $C_1$–$C_6$ alkyl and $C_1$–$C_6$ hydroxyalkyl radicals.

In one embodiment, the at least one composition may comprise, in addition to the at least one fluorescent dye, at least one additional non-fluorescent direct dye chosen from nonionic, cationic and anionic direct dyes, which may be chosen, for example, from nitrobenzene dyes.

The following red or orange nitrobenzene direct dyes are examples of direct dyes which may be used herein as additional non-fluorescent direct dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The at least one composition disclosed herein may also comprise, in addition to or in replacement of these nitrobenzene dyes, at least one additional direct dye chosen from yellow, green-yellow, blue and violet nitrobenzene dyes, nitrobenzene dyes, azo dyes, anthraquinone dyes, naphthoquinone dyes, benzoquinone dyes, phenothiazine dyes, indigoid dyes, xanthene dyes, phenanthridine dyes and phthalocyanin dyes, and triarylmethane-based dyes.

The at least one additional direct dye may also, for example, be chosen from basic dyes. Examples of basic dyes include the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", and acidic direct dyes, for example, the dyes known in the Color Index, 3rd edition, under the names "Acid Orange 7", "Acid Orange 24", "Acid Yellow 36", Acid Red 33", "Acid Red 184", "Acid Black 2", "Acid Violet 43" and "Acid Blue 62", and cationic direct dyes such as those described in patent documents WO 95/01772, WO 95/15144 and EP 714 954, the content of which relating to such cationic direct dyes is incorporated herein by reference.

The yellow and green-yellow nitrobenzene direct dyes that may be used, for example, may be chosen from the following compounds:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

The blue and violet nitrobenzene direct dyes that may be used, may for example, be chosen from the following compounds:
1-(β-hydroxyethyl)amino-4-N,N-bis(β-hydroxyethyl) amino-2-nitrobenzene,
1-(γ-hydroxypropyl)amino-4, N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene,
2-nitroparaphenylenediamines having the following formula:

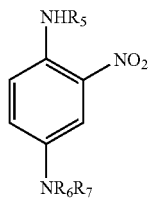

wherein:

$R_6$ is chosen from $C_1$–$C_4$ alkyl radicals and β-hydroxyethyl, β-hydroxypropyl and γ-hydroxypropyl radicals;

$R_5$ and $R_7$, which may be identical or different, are each chosen from β-hydroxyethyl, β-hydroxypropyl, γ-hydroxypropyl and β,γ-dihydroxypropyl radicals, wherein at least one of the radicals $R_6$, $R_7$ or $R_5$ is a γ-hydroxypropyl radical and $R_6$ and $R_7$ are not simultaneously a β-hydroxyethyl radical when $R_5$ is a γ-hydroxypropyl radical, such as those described in patent document FR 2 692 572.

The at least one additional direct dye, if present, is present in an amount ranging from 0.0005% to 12% by weight, relative to the total weight of the at least one composition, and, for example, from 0.005% to 6% by weight, relative to the total weight of the composition.

The at least one composition disclosed herein may also comprise at least one adjuvant chosen from various conventionally used adjuvants. For example, the at least one adjuvant may be chosen from anionic, cationic, nonionic, amphoteric and zwitterionic surfactants, anionic, cationic, nonionic, amphoteric and zwitterionic polymers, mineral thickeners, antioxidants, penetrating agents, sequestering agents, fragrances, buffers, dispersants, conditioners, film-forming agents, ceramides, preserving agents, stabilizers and opacifiers.

When surfactants are present, nonionic, anionic and/or amphoteric surfactants may, for example, be used. These surfactants may, for example, be chosen from at least one of alkyl sulphates, alkyl ether sulphates, betaines, imidazolium derivatives, alkylpyrrolidones, oxyalkylenated and glycerolated fatty alkyl ethers, fatty acid esters of monoalcohols and of polyols, optionally oxyalkylenated and glycerolated. For example, the surfactants may be present in an amount ranging from 0.01% to 30% by weight, for example, from 0.1% to 20% by weight, and, further, for example, from 0.2% to 10% by weight, relative to the total weight of the at least one composition.

The at least one composition may further comprise at least one thickener. For example, the at least one thickener may be chosen from thickening systems based on associative polymers that are well known to those skilled in the art, for example, nonionic, anionic, cationic and amphoteric thickeners. For example, the at least one thickener may be chosen from crosslinked acrylic acid homopolymers; partially and totally neutralized crosslinked homopolymers and copolymers of 2-acrylamido-2-methylpropanesulphonic acid; ammonium acrylate homopolymers and copolymers; quaternized dimethylaminoethyl methacrylate homopolymers and copolymers; nonionic guar gums, biopolysaccharide gums of microbial origin (scleroglucan gum and xanthan gum), derived from plant exudates (gum arabic, ghatti gum, karaya gum and gum tragacanth); hydroxypropyl and carboxymethyl cellulose; pectins; and alginates.

The at least one thickener, if present, is present in an amount ranging from 0.01% to 10% by weight, and, for example, from 0.1% to 5% by weight, relative to the total weight of the composition.

It should furthermore be noted that the composition disclosed herein may comprise at least one conditioning agent. For example, the at least one conditioning agent may be chosen from cations, volatile and non-volatile, modified and unmodified silicones, oils, associative polyurethane derivatives, associative cellulose derivatives, associative polyvinyllactam derivatives and associative unsaturated polyacid derivatives.

If present, the at least one conditioning agent is present in an amount ranging from 0.0025% to 10% by weight, and further, for example, from 0.025% to 10% by weight, relative to the total weight of the composition.

Needless to say, a person skilled in the art will take care to select this or these optional additional compound(s) such that the advantageous properties intrinsically associated with the composition disclosed herein is not, or are not substantially, adversely affected by the envisaged addition(s).

The composition disclosed herein may be in various forms such as in a form chosen from liquids, shampoos, creams, gels, and any other suitable form.

In one embodiment, the composition disclosed herein is in the form of a lightening dye shampoo comprising, in a cosmetically acceptable aqueous medium, at least one fluorescent dye that is soluble in the medium.

As has been mentioned above, the process of dyeing human keratin fibers with a lightening effect as disclosed herein comprises:

a) applying to said keratin fibers at least one composition comprising, in a cosmetically acceptable medium, at least one fluorescent dye that is soluble in the medium;

b) leaving the at least one composition on the keratin fibers to act for a time period sufficient to develop desired coloration and lightening;

b) optionally rinsing the keratin fibers;

c) optionally washing the keratin fibers with shampoo and optionally rinsing the keratin fibers; and d) drying or leaving to dry the keratin fibers.

As used herein, the term "human keratin fibers" means the hair. For example, the process disclosed herein may be used for treating hair which has been artificially dyed or pigmented.

As used herein, the expression "artificially dyed or pigmented hair" means hair whose tone height is less than or equal to 6 (dark blond) and, for example, less than or equal to 4 (chestnut-brown).

The lightening of the hair is evaluated by the "tone height", which describes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des Traitements Capillaires [Hair Treatment Sciences]" by Charles Zviak, 1988, published by Masson, pp. 215 and 278; the disclosure relating to this definition and classification are incorporated herein by reference.

The tone heights range from 1 (black) to 10 (light blond), one unit corresponding to one tone; the higher the figure, the lighter the shade.

Prior to the process of dyeing with a lightening effect, the fibers have undergone a permanent reshaping process.

According to one embodiment, the reshaping treatment comprises:
a) applying at least one alkaline aqueous composition with a pH of at least 10 to the keratin fibers, while smoothing out the keratin fibers;
b) leaving the at least one alkaline aqueous composition on the keratin fibers for a time period that is sufficient to shape the keratin fibers; and
c) optionally rinsing the keratin fibers, washing the keratin fibers with shampoo, rinsing the keratin fibers again, and optionally drying the keratin fibers.

The at least one alkaline aqueous composition is an aqueous solution comprising at least one alkali metal hydroxide, for example, sodium hydroxide.

It should be noted that the at least one alkaline aqueous composition may, for example, be provided in the form of an oil-in-water emulsion, the oily phase comprising, for example, liquid petroleum jelly.

The at least one alkali metal hydroxide may be present in an amount ranging from 1% to 4% by weight of the composition used during step (a).

Usually, step (a) is performed at room temperature.

The leave-in time may, for example, range from 3 to 30 minutes and, for example, from 5 to 15 minutes.

In another embodiment, the reshaping treatment comprises:
a) applying at least one reducing composition comprising, in a cosmetically acceptable medium, at least one reducing agent to the keratin fibers;
b) leaving the at least one reducing composition on the keratin fibers for a time period that is sufficient to shape them;
c) rinsing the keratin fibers;
d) applying at least one oxidizing composition;
e) leaving the at least one oxidizing composition on the keratin fibers for a time period that is sufficient to fix the shape of the keratin fibers; and
f) optionally rinsing the keratin fibers, washing the keratin fibers with shampoo, rinsed the keratin fibers and optionally drying the keratin fibers.

The at least one reducing composition used in step (a) of this process usually comprises, at least one reducing agent, chosen from thiols such as thioglycolic acid and thiolactic acid, salts thereof and esters thereof, cysteine, cysteamine and derivatives thereof, sulphites and bisulphites, for example, alkali metal, alkaline-earth metal and ammonium sulphites and bisulphites.

The at least one reducing agent may be present in an amount ranging from 1% to 30% by weight and, further, for example, from 5% to 20% by weight, relative to the total weight of the at least one reducing composition.

In general, the medium for the at least one reducing composition may be chosen from water and mixtures of water and at least one cosmetically acceptable solvent. The solvents listed in the context of the composition comprising the at least one fluorescent dye may be used.

The solvent content may, for example, not be more than 20% by weight relative to the weight of the at least one reducing composition.

The at least one reducing composition may also comprise at least one additive chosen from those commonly used by those skilled in the art. For example, the at least one additive may be chosen from nonionic, anionic, cationic and amphoteric surfactants, such as, alkyl sulphates, alkylbenzene sulphates, alkyl ether sulphates, alkylsulphonates, quaternary ammonium salts, alkylbetaines, oxyethylenated alkylphenols, fatty acid alkanolamides, oxyethylenated fatty acid esters, and also other nonionic surfactants of the hydroxypropyl ether type.

When the at least one reducing composition comprises at least one additive of this type, the at least one additive may be present in an amount equal to less than 30% by weight and, further, for example, ranging from 0.5% to 10% by weight, relative to the total weight of the at least one reducing composition.

The at least one reducing composition may be provided in a form chosen from thickened and non-thickened lotions, creams, gels, and other suitable forms.

When the at least one reducing composition is intended for relaxing and/or straightening the hair, the at least one reducing composition may, for example, be in the form of a thickened cream so as to keep the hair as straight as possible. These creams are made in the form of "heavy" emulsions, obtained, for example, by emulsifying an aqueous phase, for example, comprising the at least one reducing agent, and an oily phase (plant oil, liquid paraffin, fatty acid esters or wax, for example).

Liquids or gels comprising thickeners, such as carboxyvinyl polymers or copolymers that "stick" the hairs together and hold them in the smooth position during the leave-in time, may also be used.

If the process is intended to make the fibers curly, these fibers are placed under tension using curlers, before, during or after applying the composition.

The leave-in time may, for example, range from 3 to 30 minutes, for example, from 5 to 15 minutes.

The at least one oxidizing composition used during step (d) conventionally comprises at least one oxidizing agent, for example, chosen from aqueous hydrogen peroxide solution, alkali metal bromate, persalt and polythionate.

The pH of the at least one oxidizing composition may, for example, range from 2 to 10.

The leave-in time may, for example, range from 3 to 30 minutes and, for example, from 5 to 15 minutes.

For example, the hair impregnated with the at least one oxidizing composition may be rinsed thoroughly, generally with water. Before or after rinsing, the keratin fibers may be separated from the means required to keep them under tension.

The dyeing process may be performed on dry or wet fibers, immediately or not immediately after the reshaping process.

In one embodiment, the dyeing process disclosed herein comprises applying at least one composition as defined above to the fibers, for example, hair, for a time period that is sufficient to develop the desired coloration and lightening, rinsing the fibers, optionally washing the fibers with shampoo, rinsed again and drying the fibers.

The time period required to develop the coloration and to obtain the lightening effect on the fibers, for example, the hair, may range from 5 to 60 minutes and, for example, from 5 to 40 minutes.

The temperature required to develop the coloration and to obtain the lightening effect may, for example, range from room temperature (15 to 25° C.) to 80° C. and, for example, from 15 to 40° C.

It should be noted that the at least one composition disclosed herein, if used to treat keratin fibers, such as chestnut-brown hair, may make it possible to achieve at least one of the following results:

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it was found that the reflectance curve corresponding to the treated hair, in a wavelength range from 500 to 700 nanometers, was higher than that corresponding to the untreated hair.

This means that, in the wavelength range from 500 to 700 nanometers, and for example, from 540 to 700 nanometers, there is at least one range in which the reflectance curve corresponding to the treated hair is higher than the reflectance curve corresponding to the untreated hair. As used herein, the term "higher than" means a difference of at least 0.05% and, for example, of at least 0.1% of reflectance.

However, it is pointed out that there may be, within the wavelength range from 500 to 700 nanometers and, for example, from 540 to 700 nanometers, at least one range wherein the reflectance curve corresponding to the treated fibers is either superimposable on or lower than the reflectance curve corresponding to the untreated fibers.

For example, the wavelength at which the difference is maximal between the reflectance curve for the treated hair and that for the untreated hair is in the wavelength range from 500 to 650 nanometers and, for example, in the wavelength range from 550 to 620 nanometers.

Further, for example, the at least one composition may be capable of lightening the hair and the skin in a shade which, measured in the CIEL L*a*b* system, has a variable b* of greater than or equal to 6, with a b*/absolute value of a* ratio of greater than 1.2 according to the selection test described below.

Selection Test

The composition was applied to chestnut-brown keratin fibers, for example, the hair, at a rate of 10 grams of composition per 1 gram of chestnut-brown fibers. The composition was spread on so as to cover all of the fibers. The composition was left to act for 20 minutes at room temperature (20 to 25° C.). The fibers were then rinsed with water and then washed with a shampoo based on lauryl ether sulphate. They were then dried. The spectrocolorimetric characteristics of the fibers were then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following example is intended to illustrate the invention without limiting the scope as a result.

EXAMPLE

A water-in-liquid petroleum jelly emulsion comprising a sodium hydroxide solution at 3% by weight was applied to a lock of African hair, while smoothing it out, for 15 minutes, after which the lock was rinsed thoroughly.

The composition below, prepared in accordance with the present disclosure, was then applied:

| | |
|---|---|
| Fluorescent compound (*) | 0.6% |
| Sodium N-cocoylamidoethyl-N-ethoxycarboxymethylglycinate | 2% |
| Hexylene glycol | 7% |
| Distilled water qs | 100 g |

The percentages are expressed as the weight of active material.
(*) Fluorescent compound:

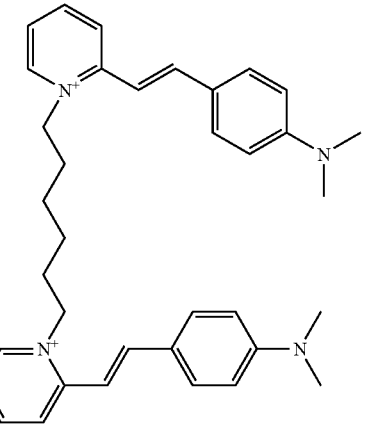

This compound was obtained according to the method below:

93 g of 2-picoline were reacted with 120 g of 1,6-dibromohexane in dimethylformamide at 110° C. for 5 hours.

The precipitated product was recovered and filtered off.

109 g of the product obtained above was dissolved in methanol and 82.82 g of p-dimethylaminobenzaldehyde was added in two portions, in the presence of pyrrolidine.

The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4 \cdot 2Br$.

The composition was applied to the treated lock, with a leave-in time of 20 minutes. The lock was then rinsed and dried under a hood for 30 minutes.

A marked lightening of the lock of hair was obtained.

What is claimed is:

1. A process for dyeing, with a lightening effect, human keratin fibers that have previously been subjected to a permanent reshaping process and have a tone height of less than or equal to 6, comprising:
    a) applying to said keratin fibers, in an amount effective to provide a lightening effect on fibers that have previously been subjected to a permanent reshaping process and have a tone height of less than or equal to 6, at least one composition comprising, in a cosmetically acceptable medium, at least one fluorescent dye that is soluble in the medium, wherein the at least one fluorescent dye is chosen from compounds of the following formulae:

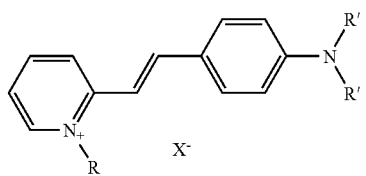

wherein R is chosen from methyl and ethyl radicals, R' is a methyl radical, and X⁻ is chosen from anions;

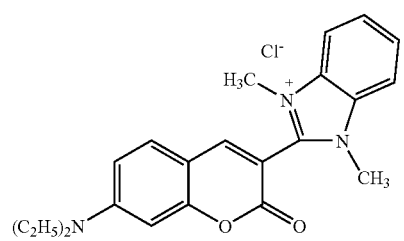

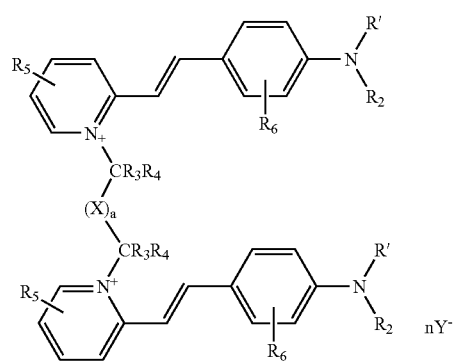

wherein:
$R_1$ and $R_2$, which may be identical or different, are each chosen from:
  a hydrogen atom;
  linear and branched alkyl radicals comprising from 1 to 10 carbon atoms, wherein said alkyl radicals are optionally interrupted and/or substituted with at least one entity chosen from hetero atoms and from groups comprising at least one hetero atom and/or wherein said alkyl radicals are substituted with at least one halogen atom;
  aryl and arylalkyl radicals, wherein the aryl group comprises 6 carbon atoms and the alkyl group comprises from 1 to 4 carbon atoms, and wherein the aryl radical is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and from groups comprising at least one hetero atom and/or wherein the at least one alkyl radical is substituted with at least one halogen atom;

$R_1$ and $R_2$ may optionally form, together with the nitrogen atom to which they are attached, a heterocycle and may comprise at least one other hetero atom, wherein the heterocycle is optionally substituted with at least one alkyl radical chosen from linear and branched alkyl radicals, wherein said at least one alkyl radical is optionally interrupted and/or substituted with at least one entity chosen from hetero atoms and from groups comprising at least one hetero atom and/or is substituted with at least one halogen atom; and $R_1$ or $R_2$ may optionally form, together with the nitrogen to which they are attached and one of the carbon atoms of the phenyl group bearing the nitrogen atom, a heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and from groups bearing at least one hetero atom and/or wherein the alkyl radicals are substituted with at least one halogen atom;

X is chosen from:
  linear and branched alkyl radicals comprising from 1 to 14 carbon atoms and alkenyl radicals comprising from 2 to 14 carbon atoms, wherein the alkyl radicals and the alkenyl radicals are optionally interrupted and/or substituted with at least one entity chosen from hetero atoms and from groups comprising at least one hetero atom and/or wherein the radicals are substituted with at least one halogen atom;
  5- or 6-membered heterocyclic radicals optionally substituted with at least one alkyl radical chosen from linear and branched alkyl radicals comprising from 1 to 14 carbon atoms, wherein the at least one alkyl radical is optionally substituted with at least one entity chosen from hetero atoms; with linear and branched aminoalkyl radicals comprising from 1 to 4 carbon atoms, optionally substituted with at least one hetero atom; and/or with at least one halogen atom;
  fused and non-fused aromatic and diaromatic radicals, optionally separated with at least one alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
  a dicarbonyl radical; and
  wherein the group X possibly bears at least one cationic charge;

a is equal to 0 or 1;

$Y^-$, which may be identical or different, is chosen from organic and mineral anions; and n is an integer equal to at least 2 and at most equal to the number of cationic charges present in the at least one fluorescent dye;

b) leaving the at least one composition on the keratin fibers to act for a time period sufficient to develop desired coloration and lightening;

b) optionally rinsing the keratin fibers;

c) optionally washing the keratin fibers with shampoo and optionally rinsing the keratin fibers; and d) drying or leaving to dry the keratin fibers.

2. The process according to claim 1, wherein the at least one fluorescent dye has a reflectance maximum in the wavelength range of from 500 nm to 650 nm.

3. The process according to claim 2, wherein the at least one fluorescent dye has a reflectance maximum that is in the wavelength range of from 550 nm to 620 nm.

4. The process according to claim 1, wherein the at least one fluorescent dye is chosen from dyes in the orange range.

5. The process according to claim 1, wherein, in formula (F1), $X^-$ is chosen from iodide, sulphate, and methosulphate anions.

6. The process according to claim 5, wherein, in formula (F4), $R_1$ and $R_2$, which may be identical or different, are each chosen from linear and branched alkyl radicals comprising from 1 to 4 carbon atoms.

7. The process according to claim 6, wherein, in formula (F4), the heterocycle formed from $R_1$ and $R_2$ and the nitrogen to which they are attached, is optionally substituted with at least one alkyl radical chosen from linear and branched alkyl radicals comprising from 1 to 4 carbon atoms.

8. The process according to claim 1, wherein the at least one fluorescent dye is present in an amount ranging from 0.01% to 20% by weight, relative to the total weight of the at least one composition.

9. The process according to claim 8, wherein the at least one fluorescent dye is present in an amount ranging from 0.05% to 10% by weight, relative to the total weight of the at least one composition.

10. The process according to claim 9, wherein the at least one fluorescent dye is present in an amount ranging from 0.1% to 5% by weight, relative to the total weight of the at least one composition.

11. The process according to claim 1, wherein the at least one fluorescent dye is soluble in the medium of the at least one composition to at least 0.001 g/l at a temperature ranging from 15 to 25° C.

12. The process according to claim 11, wherein the at least one fluorescent dye is soluble in the medium of the at least one composition to at least 0.5 g/l at a temperature ranging from 15 to 25° C.

13. The process according to claim 12, wherein the at least one fluorescent dye is soluble in the medium of the at least one composition to at least 1 g/l at a temperature ranging from 15 to 25° C.

14. The process according to claim 13, wherein the at least one fluorescent dye is soluble in the medium of the at least one composition to at least 5 g/l at a temperature ranging from 15 to 25° C.

15. The process according to claim 1, wherein the at least one composition further comprises at least one surfactant chosen from nonionic, anionic and amphoteric surfactants.

16. The process according to claim 15, wherein the at least one surfactant is present in an amount ranging from 0.01% to 30% by weight, relative to the total weight of the at least one composition.

17. The process according to claim 1, wherein the at least one composition further comprises at least one additional non-fluorescent direct dye chosen from nonionic, cationic and anionic non-fluorescent direct dyes.

18. The process according to claim 1, wherein the at least one additional non-fluorescent direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, and triaryl-methane-based dyes.

19. The process according to claim 18, wherein the at least one additional non-fluorescent direct dye is present in an amount ranging from 0.0005% to 12% by weight, relative to the total weight of the at least one composition.

20. The process according to claim 19, wherein the at least one additional non-fluorescent direct dye is present in an amount ranging from 0.005% to 6% by weight, relative to the total weight of the at least one composition.

21. The process according to claim 1, wherein the at least one composition is provided in a form of a lightening dyeing shampoo.

22. The process according to claim 1, comprising, before applying the at least one composition to the keratin fibers:

a) applying at least one alkaline aqueous composition with a pH of at least 10 to the keratin fibers, while smoothing out the keratin fibers;

b) leaving the at least one alkaline aqueous composition on the keratin fibers for a time period that is sufficient to shape the keratin fibers; and c) optionally rinsing the keratin fibers, washing the keratin fibers with shampoo, rinsing the keratin fibers again, and optionally drying the keratin fibers.

23. The process according to claim 1, comprising, before applying the at least one composition to the keratin fibers:

a) applying at least one reducing composition comprising, in a cosmetically acceptable medium, at least one reducing agent to the keratin fibers;

b) leaving the at least one reducing composition on the keratin fibers for a time period that is sufficient to shape them;

c) rinsing the keratin fibers;

d) applying at least one oxidizing composition;

e) leaving the at least one oxidizing composition on the keratin fibers for a time period that is sufficient to fix the shape of the keratin fibers; and f) optionally rinsing the keratin fibers, washing the keratin fibers with shampoo, rinsed the keratin fibers and optionally drying the keratin fibers.

24. The process according to claim 1, wherein the at least one composition is applied to hair with a tone height of less than or equal to 4.

25. The process according to claim 1, wherein the human keratin fibers are artificially dyed or pigmented.

* * * * *